United States Patent [19]

Kershner et al.

[11] Patent Number: 4,910,309

[45] Date of Patent: Mar. 20, 1990

[54] ENRICHMENT OF OPTICAL PURITY OF 2-(4-ARYLOXYPHENOXY)-PROPIONIC ACIDS BY CRYSTALLIZATION AS HYDRATES

[75] Inventors: Larry D. Kershner; Jimmy J. Tai, both of Midland, Mich.

[73] Assignee: The Dow Chemical Company, Midland, Mich.

[21] Appl. No.: 216,598

[22] Filed: Jul. 8, 1988

[51] Int. Cl.$^4$ .................. C07D 241/44; C07D 213/64; C07D 213/58
[52] U.S. Cl. .................................... 544/354; 546/301; 546/302; 548/217; 548/221; 558/354; 558/414; 562/401; 562/402; 562/471
[58] Field of Search ................ 544/354; 546/301, 302; 548/217, 221; 562/401, 402, 471; 558/354, 414

[56] References Cited

U.S. PATENT DOCUMENTS 3,857,889 12/1974 Leigh .............................. 260/570.7

OTHER PUBLICATIONS

Collet et al., *Chem. Rev.* 80, pp. 215–230 (1980).
"Enantiomers, Racemates, and Resolutions," by Jacques et al. (Wiley & Sons, N.Y.), pp. 217–250, (1980).

*Primary Examiner*—Nicholas S. Rizzo
*Assistant Examiner*—E. Bernhardt
*Attorney, Agent, or Firm*—Craig E. Mixan; Ronald G. Brookens

[57] ABSTRACT

The optical purity of an optically active 2-(4-aryloxyphenoxy)propionic acid is enriched by formation of the hydrate of the enantiomer in excess and its removal from solution.

9 Claims, No Drawings

ENRICHMENT OF OPTICAL PURITY OF 2-(4-ARYLOXYPHENOXY)-PROPIONIC ACIDS BY CRYSTALLIZATION AS HYDRATES

FIELD OF THE INVENTION

The present invention is directed to enriching the optical purity of optically active 2-(4-aryloxyphenoxy)-propionic acids. More specifically, the present invention is directed to enriching the optical purity of optically active 2-(4-aryloxyphenoxy)propionic acids by crystallization as hydrates.

BACKGROUND OF THE INVENTION

The herbicidal activity of 2-(4-aryloxyphenoxy)propionic acids and derivatives thereof is well known in the art. Furthermore, optical isomers are often known to exhibit enhanced herbicidal activity over the corresponding racemates. For example, U.S. Patent No. 4,531,969 discloses that the R-enantiomers of certain 2-(4-aryloxyphenoxy)propionic acids and certain derivatives thereof are distinguished by a considerably enhanced herbicidal action compared to the racemic modifications. Since reduced quantities of herbicide are required to achieve comparable levels of control, the application of mixtures enriched in the more efficacious R-enantiomer offers both economical and environmental advantages.

To exploit the agronomic benefits of these advantages, it is necessary to efficiently resolve racemic mixtures of herbicides that are normally produced industrially. Various methods for obtaining high concentrations of individual enantiomers are known. For example, individual enantiomers can be obtained by direct synthesis employing appropriate optically active starting materials. Alternatively, a racemate can be resolved by conversion with an optically active reagent into a mixture of diastereomers which can subsequently be separated on the basis of their different physical properties. Theoretically, one can obtain essentially 100 percent of the desired enantiomers by these methods. In practice, however, the products typically contain from 70 to 95 percent of the desired enantiomer and, correspondingly, from 5 to 30 percent of the other optical isomer. Such products are then said to possess an optical purity of 40 to 90 percent, i.e., from 40 to 90 percent of the mixture is the desired enantiomer and from 10 to 60 percent is a racemic mixture.

An efficient technique for the continued enrichment of mixtures already containing an excess of a particular enantiomer is resolution by entrainment, otherwise known as preferential crystallization. Unlike other resolution methods, entrainment does not require an auxiliary chiral compound such as, for example, an optically active reagent to form diastereomers or an optically active solvent, in order to achieve an effective resolution. The principles of enantiomer resolution by direct crystallization, particularly by entrainment, have been reviewed by J. Jacques et al. in *Enantiomers, Racemates, and Resolutions*, John Wiley & Sons, Inc., New York, N.Y., 1980, Chapter 4, pages 223–241.

SUMMARY OF THE INVENTION

A new method for enriching the optical purity of a 2-(4-aryloxyphenoxy)propionic acid already containing a preponderance of the herbicidally more efficacious R-enantiomer has been discovered. The method, which is based on the preferential formation of the hydrate of the enantiomeric acid in excess, advantageously does not require an auxiliary chiral reagent or solvent. More specifically, the present invention is directed to a process for enriching the optical purity of an optically active 2-(4-aryloxyphenoxy)propionic acid of Formula (I)

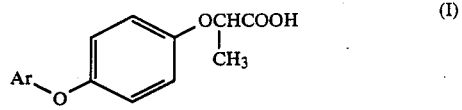

wherein
Ar is an unsubstituted phenyl, a substituted phenyl, pyridinyl, quinoxalinyl or benzoxazolyl ring system
which comprises treating an organic solution of the 2-(4-aryloxyphenoxy)propionic acid having an excess of one enantiomer with at least one equivalent of water to form a hydrate of the enantiomer in excess, and separating the hydrate from the solution.

DETAILED DESCRIPTION OF THE INVENTION

The 2-(4-aryloxyphenoxy)propionic acids to which the present method may be applied are disclosed, for example, in U.S. Pat. Nos. 4,046,553, 4,332,960, 4,332,961, 4,477,276, 4,523,017, 4,531,969, 4,550,192, 4,565,568, 4,600,432, 4,609,396 and 4,629,493 and European Patent Application Publication Nos. 483, 1,473 and 3,890.

Particularly valuable examples of 2-(4-aryloxyphenoxy)propionic acids to which the present method may be applied are of Formula (II)–(V):

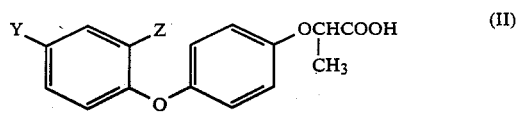

wherein
Y is halogen, $CF_3$ or CN and
Z is H or halogen:

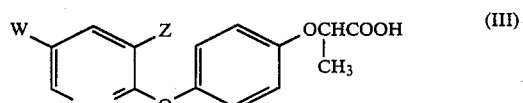

wherein
W is $CF_3$ or halogen and
Z is as previously defined;

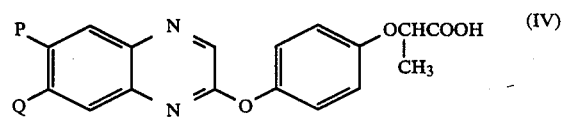

wherein
P and Q each are independently H or halogen; and

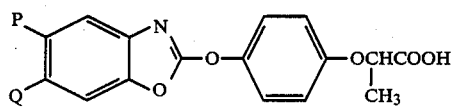

wherein

P and Q are as previously defined.

For compounds of Formula (II), Y is preferably $CF_3$, Br, I or CN and Z is preferably F or Cl.

For compounds of Formula (III), W is preferably $CF_3$, Cl, Br or I and Y is preferably H, F or Cl.

For compounds of Formula (IV), one of P or Q is preferably F or Cl.

For compounds of Formula (V), one of P or Q is preferably F or Cl.

This does not imply that the present process works equally well with all of the compounds disclosed above. Differences in physical properties may allow hydrate formation and separation to vary from compound to compound resulting in significantly different efficiencies. Compounds of Formulas (II) and (III) wherein Y is halogen, Z is hydrogen or halogen and W is $CF_3$ or halogen are well-suited for the present enrichment process.

As used herein, the term "halogen refers to F, Cl, Br or I.

The excess of a particular enantiomer in the original optically active 2-(4-aryloxyphenoxy)propionic acid to be enriched can range from 60 to 99 percent, i.e., optical purities of from 20 to 98 percent. The present method is particularly effective for enriching the optical purity of samples which are already of relatively high optical purity, e.g., from about 90 to 98 percent optically pure. In this range, not only is an (aryloxyphenoxy)propionic acid of very high optical purity obtained, but the propionic acid is recovered in relatively higher yield than when less substantial excesses of a particular enantiomer are employed.

In a typical operation, the optically active 2-(4-aryloxyphenoxy)propionic acid can be dissolved in an organic solvent which is capable of dissolving and preferably crystallizing the propionic acid and which should be, to a great extent, immiscible with water. Aromatic hydrocarbons and halogenated aliphatic or aromatic hydrocarbons are particularly useful solvents for the present method.

Once dissolution is complete, anhydrous racemate or material of lesser optical purity than that initially employed can optionally be removed by cooling and subsequent filtration. To isolate the hydrate of the enantiomer in excess, at least one equivalent of water based on the amount of acid present can be added to the solution with agitation and the mixture can be cooled. The material that crystallizes as the hydrate can be isolated by routine techniques such as filtration or centrifugation which are typically used to recover solid products.

The anhydrous 2-(4-aryloxyphenoxy)propionic acid can be recovered from the hydrate by conventional dehydration procedures.

The following examples further illustrate the present invention and are not to be construed as a limitation thereon.

EXAMPLE 1

Enrichment of the Optical Purity of R-2-(4-(2'-fluoro-4'-bromophenoxy)phenoxy)propionic acid by Crystallization as the Hydrate A dry solution of 100 grams (g) of R-2-(4-(2'-fluoro-4'-bromophenoxy)phenoxy)propionic acid (96 percent R) in 300 milliliters (mL) of toluene was prepared by heating the mixture to reflux and azeotropically removing the water from the solution. The solution was cooled to about 10° C. and the solid which formed was removed by filtration. Water 20 grams (g) was then added to the solution which was stirred at 10° C. for one hour (hr). The resulting crystals (53 g) of monohydrate were isolated by filtration. Enantiomeric analysis indicated an optical purity of 99.4 percent R-enantiomer.

EXAMPLE 2

Enrichment of the Optical Purity of R-2-(4-((3'-fluoro-5'-trifluoromethyl-2'-pyridinyl)oxy)phenoxy)propionic acid by Crystallization as the Hydrate The methyl ester of R-2-(4-(3'-fluoro-5'-trifluoromethyl-2'-pyridinyl)oxy)phenoxy)propionic acid 100 g; R/S=95/5) was added to 278 g of 5 percent NaOH solution and the mixture was heated to 40° C. When hydrolysis was complete, the pH was adjusted to approximately 1.0 to precipitate the acid from solution. The acid was isolated by filtration and was dissolved in 400 mL of perchloroethylene. Residual water was removed by distillation and the solution was cooled to 15° C. About 17 g of anhydrous acid having an R to S ratio of 73/27 was collected by filtration. The filtrate was treated with 40 mL of water and was kept at 15° C. for 2 hr. A total of 82 g of monohydrate having an optical purity of 99.5 percent was collected.

EXAMPLE 3

Preparation of R-2-(4-((3'-chloro-5'-trifluoromethyl-2'-pyridinyl)oxy)phenoxy)propionic acid 2,3-Dichloro-5-trifluoromethylpyridine (43.2 g) and R-2-(4-hydroxyphenoxy)propionic acid (36.4 g: R/S =97/3) were added to 200 mL of dimethylsulfoxide. Potassium carbonate (66.4 g) was added to the solution and the temperature was raised to 85° C. and maintained there for 3 hr. After cooling to ambient temperature, the solids were removed by filtration and 400 mL of water were added to the filtrate. The pH of the mixture was adjusted to 1.0 and the product was extracted from the aqueous mixture with methyl iso-butyl ketone. After evaporation of the solvent, the crude product was dissolved in 80 mL of perchloroethylene. Water (20 mL) was added to the solution which was chilled to −4° C. overnight. A total of 22 g of hydrate having an optical purity greater than 99.8 percent was collected by filtration.

Various modifications may be made in the present invention without departing from the spirit or scope thereof, and it is understood that I limit myself only as defined in the appended claims.

What is claimed is:

1. A process for enriching the optical purity of an optically active 2-(4-aryloxyphenoxy)propionic acid of Formula (I)

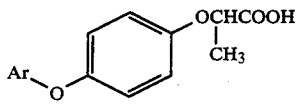

(I)

wherein

Ar is a phenyl, pyridinyl, quinoxalinyl or benzoazolyl ring system substituted with one or two substituents independently selected from the group consisting of halogen, $CF_3$ and CN, which comprises treating an organic solution of the 2-(4-aryloxyphenoxy)propionic acid having an excess of one enantiomer with at least one equivalent of water to form a hydrate of the enantiomer in excess, and separating the hydrate from the solution.

2. The process of claim 1 wherein Ar represents a substituted phenyl group of the formula

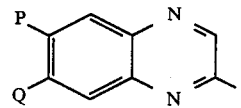

in which
Y is halogen, $CF_3$ or CN and
Z is hydrogen or halogen.

3. The process of claim 1 wherein Ar

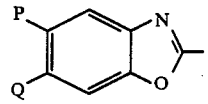

in which

W is $CF_3$ or halogen and
Z is hydrogen or halogen.

4. The process of claim 1 wherein Ar represents a quinoxalinyl group of formula in which P and Q are each independently H or halogen, provided one of P or Q is halogen.

5. The process of claim 1 wherein Ar represents a benzoxazolyl group of formula wherein P and Q are each independently H or halogen, provided one of P or Q is halogen.

6. The process of claim 2 wherein Y is halogen and Z is halogen.

7. The process of claim 3 wherein W is $CF_3$ and Z is hydrogen or halogen.

8. The process of claim 1 wherein the optical purity of the 2-(4-aryloxyphenoxy)propionic acid to be enriched is from about 90 to about 98 percent.

9. The process of claim 1 wherein the organic solution is prepared by dissolving the 2-(4-aryloxyphenoxy)propionic acid in an organic solvent selected from the group consisting of aromatic hydrocarbons, halogenated aliphatic hydrocarbons and halogenated aromatic hydrocarbons.

* * * * *